United States Patent
Nielsen et al.

(10) Patent No.: US 8,951,741 B1
(45) Date of Patent: Feb. 10, 2015

(54) **DIAGNOSIS OF *STRONGYLUS VULGARIS***

(71) Applicant: University of Kentucky Research Foundation, Lexington, KY (US)

(72) Inventors: Martin Nielsen, Lexington, KY (US); Ulla Anderson, Hoersholm (DK); Daniel Howe, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 14/066,390

(22) Filed: Oct. 29, 2013

Related U.S. Application Data

(60) Provisional application No. 61/719,762, filed on Oct. 29, 2012.

(51) Int. Cl.
| | |
|---|---|
| *G01N 33/00* | (2006.01) |
| *G01N 33/53* | (2006.01) |
| *G01N 33/554* | (2006.01) |
| *G01N 33/567* | (2006.01) |
| *G01N 33/569* | (2006.01) |
| *C07K 14/435* | (2006.01) |

(52) U.S. Cl.
CPC .... *G01N 33/56966* (2013.01); *C07K 14/43536* (2013.01)
USPC ............ 435/7.1; 435/7.2; 435/7.32; 435/7.92

(58) Field of Classification Search
None
See application file for complete search history.

(56) References Cited

PUBLICATIONS

Adeyefa, C.A.O., 1992. Precipitin response of the mitogen produced by *Strongylus vulgaris* arterial larvae. Vet. Parasitol. 43, 243-247.
Hassan, S.E., Ghazy, A.A., Abdel-Rahman, E.H., 2010. Isolation and characterization of immunodiagnostic antigen from *Strongylus vulgaris* infecting horses. World Appl. Sci. J. 8, 235-240.
Klei, T.R., Chapman, M.R., Torbert, B.J., McClure, J.R., 1983. Antibody responses of ponies to initial and challenge infections of *Strongylus vulgaris*. Vet. Parasitol. 12, 187-198.
Nichol, C., Masterson, W.J., 1987. Characterisation of surface antigens of *Strongylus vulgaris* of potential immunodiagnostic importance. Mol. Biochem. Parasitol. 25, 29-38.
Wynne, E., Slocombe, J.O.D., Wilkie, B.N., 181. Antigenic Analysis of Tissues and Excretory and Secretory Products from *Strongylus vulgaris*. Can. J. Comp. Med. 45, 259-265.
Chandrashekar, R., Curtis, K.C., Ramzy, R.M., Liftis, F., Li, B.W., Weil, G.J., 1994. Molecular cloning of *Brugia malayi* antigens for diagnosis of lymphatic filariasis. Mol. Biochem. Parasitol. 64, 261-271.
Dissanayake, S., Xu, M., Piessens, W.F., 1992. A cloned antigen for serological diagnosis of Wuchereria bancroft microfilaremia with daytime blood samples. Mol. Biochem. Parasitol. 56, 269-277.
Fujiwara, R.T., Zhan, B., Mendez, S., Loukas, A., Bueno, L.L., Wang, Y., Plieskatt, J., Oksov, Y., Lustigman, S., Bottazzi, M.E., Hotez, P., Bethony, J.M., 2007. Reduction of worm fecundity and canine host blood loss mediates protection against hookworm infection elicited by vaccination with recombinant Ac-16. Clin. Vaccine Immunol. 14, 281-287.
Lalitha, P., Eswaran, D., Gnanasekar, M., Rao, K.V., Narayanan, R.B., Scott, A., Nutman, T., Kaliraj, P., 2002. Development of antigen detection ELISA for the diagnosis of brugian and bancroftian filariasis using antibodies to recombinant filarial antigens Bm-SXP-1 and Wb-SXP-1. Microbiol Immunol 46, 327-332.
Pandiaraja, P., Arunkumar, C., Hoti, S.L., Rao, D.N., Kaliraj, P., 2010 Evaluation of synthetic peptides of WbSXP-1 for the diagnosis of human lymphatic filariasis. Diagn Microbiol Infect Dis 68, 410-415.
Rao, K.V., Eswaran, M., Ravi, V., Gnanasekhar, B., Narayanan, R.B., Kaliraj, P., Jayararnan, K., Marson, A., Raghavan, N., Scott, A.L., 2000 The Wuchereria bancroft orthologue of *Brugia malayi* SXP1 and the diagnosis of bancroftian filariasis. Mol. Biochem. Parasitol. 107, 71-80.
Wang, S., Zheng, H., Tao, Z., Piessens, W.F., 1999. [Studies on recombinant chitinase and SXP-1 antigens as antimicrofilarial vaccines]. Zhongguo ji sheng chong xue yu ji sheng chong bing za zhi=Chinese journal of parasitology & parasitic diseases 17, 90-94.
Andersen U.V., Howe D.K., Lyons E.T., Nielsen M.K., 2011: Towards diagnosing migrating *Strongylus vulgaris*: preliminaty data. 23rd International Conference of the World Association for the Advancement of Veterinary Parasitology (WAAVP), Buenos Aires, Argentina, Aug. 21-25, 2011.
Andersen U.V., Howe D.K., Olsen S.N., Monrad J., Nejsum P., Lyons E.T., Nielsen M.K. Serological diagnosis of *Strongylus vulgaris* infection: use of a recombinant protein, Annual Meeting, American Association of Veterinary Parasitologists, San Diego, CA, Aug. 4-7, 2012.
Andersen, U.V., Howe, D.K., Olsen, S.N., Monnad, J., Nejsum, P., Lyons, E.T., Nielsen, M.K. Serological diagnosis of *Strongylus vulgaris* infection. Equine Infectious Disease Conference, Lexington, KY, Oct. 21-26, 2012.
Andersen UV, Howe DK, Olsen SN, Nielsen MK: Recent advances in diagnosing pathogenic equine gastrointestinal helminths: The challenge of prepatent detection. Vet Parasitol 2013, 192(1-3):1-9.
Dowdall, S.M.J., Matthews, J.B., Mair, T., Murphy, D., Love, S., Proudman, C.J., 2002. Antigen-specific IgG(T) responses in natural and experimental cyathostominae infection in horses. Vet. Parasitol. 106, 225-242.

*Primary Examiner* — Albert Navarro
(74) *Attorney, Agent, or Firm* — Stites & Harbison PLLC; Mandy Wilson Decker; Nicolo Davidson

(57) ABSTRACT

Embodiments of the presently-disclosed subject matter provide an isolated polypeptide comprising the sequence of SEQ ID NO: 1, fragments thereof, and/or epitopes thereof. Embodiments of the presently-disclosed subject matter also provide methods for diagnosing a *Strongylus vulgaris* infection in a subject that comprises providing a biological sample from the subject and contacting the sample with the present isolated polypeptide, fragment thereof, and/or epitope thereof. In some embodiments the *Strongylus vulgaris* infection can be detected during a prepatent period. In further embodiments the subject is a horse.

13 Claims, 4 Drawing Sheets

US 8,951,741 B1

DIAGNOSIS OF *STRONGYLUS VULGARIS*

RELATED APPLICATIONS

This application claims priority from U.S. Provisional Patent Application No. 61/719,762, filed Oct. 29, 2012, the entire disclosure of which is incorporated herein by this reference.

TECHNICAL FIELD

The presently-disclosed subject matter relates to diagnosis of pathogenic parasites. In particular, the presently-disclosed subject matter relates to diagnosis of *Strongylus vulgaris* in a subject, including a horse.

INTRODUCTION

The lifecycle of *S. vulgaris* is characterized by a long prepatent period when the migrating larvae are virtually undetectable, which poses an unsolved challenge for diagnosis. Strongyle parasites are ubiquitous in grazing horses with more than 50 different species described (Lichtenfels et al., 2008). The most pathogenic of the gastrointestinal parasites infecting horses, *Strongylus vulgaris*, belongs to the large strongyles that are known for their extensive tissue migration and a long prepatent period of 6-7 months (Round, 1969). During this time, *S. vulgaris* larvae migrate in the arteries that supply large portions of the intestinal tract, with the cranial mesenteric artery and major branches being the predilection site (Enigk, 1970; Duncan and Pirie, 1972). Here, the larvae cause verminous endarteritis with aneurysm and thrombus formation, leucocytic infiltration and fibrosis of the arterial wall (Drudge et al., 1966; Duncan and Pirie, 1975; Morgan et al., 1991). The presence of the larvae can lead to a non-strangulating infarction of portions of the intestinal tract, often known as verminous thromboembolic infarction (Curtis, 1964; Enigk, 1970).

Historically, *S. vulgaris* was prevalent (80-100%) (Bollinger, 1870; Slocombe and McCraw, 1973) and a parasite control strategy, the interval dose regimen, was used to control this parasite (Drudge and Lyons, 1966). This regimen was based on knowledge of the *S. vulgaris* life cycle as well as the mechanism of action of the available anthelmintic drugs. The interval dose regimen became widely implemented, and in the past couple of decades the prevalence of *S. vulgaris* based on coprology was greatly reduced in horses that were treated regularly (Höglund et al., 1997; Pilo et al., 2011).

With the emergence of anthelmintic resistance among the cyathostomins (small strongyles) and *Parascaris equorum*, emphasis has been oriented towards an epidemiological approach to helminth control (Herd et al., 1985), with targeted selective therapy advocated to ensure anthelmintic efficacy in the future (Kaplan, 2002, 2004). In the European Union, prescription-only restrictions on anthelmintic drugs have been or are being implemented by legislation of member countries. This ensures that only a veterinarian can prescribe the anthelmintic drug after a diagnosis of parasite infection has been reached. Experiences from Denmark with prescription-only limitations and selective anthelmintic therapy show that a reduction in treatment intensity follows (Nielsen et al., 2006). Recently, it was shown that reduced treatment intensity in Denmark allow for higher prevalence of *S. vulgaris* (Nielsen et al., 2012). Thus, there exists a need for improved diagnostic assays in order to better control this parasite while maintaining anthelmintic efficacy by targeted selective therapy.

The lifecycle of *S. vulgaris* is characterized by a long prepatent period when the migrating larvae are nearly or completely undetectable, which poses an unsolved challenge for diagnosis. Currently, diagnosis of *S. vulgaris* infection is based on the presence of eggs shed by adult females in faeces of infected horses; this is accomplished currently either by larval culture and subsequent microscopic examination (Russell, 1948; Bevilaqua et al., 1993) or by a semi-quantitative PCR (Nielsen et al., 2008). So far, no test has been developed to accurately diagnose the presence of migrating larvae in the cranial mesenteric artery. Furthermore, an apparent increase in prevalence of *S. vulgaris* has been observed in regions where reduced anthelmintic treatment intensity has been implemented.

These issues highlight the need for accurate and reliable tools for prepatent diagnosis of *S. vulgaris* infection.

BRIEF DESCRIPTION OF THE DRAWINGS

(FIG. 6a: n=42; FIG. 6b: n=28); group 1: Migratory tracts or evidence of previous infection (n=16); group 2: 1-5 larvae (n=16); group 3: 6-25 larvae (n=17); and group 4: >25 larvae (FIG. 6a: n=11; FIG. 6b: n=9). The middle black line of the boxes is the median and the range of the box is the inter quartile range (IQR) giving the first and third IQR. The lower and upper lines are up to 1.5 IQR away from the first and third quartile. Groups with different letters are significantly different (P-value <0.05).

BRIEF DESCRIPTION OF THE SEQUENCE LISTINGS

Figure 1:
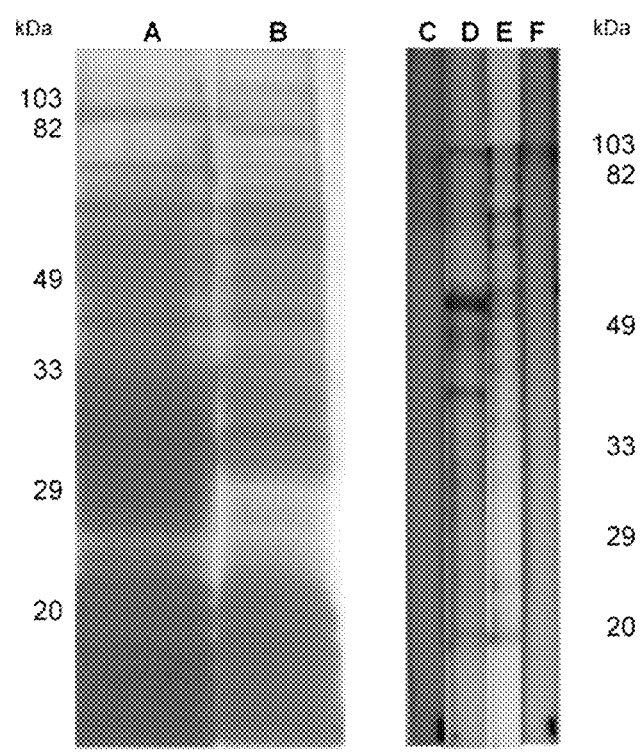
FIG. 1 includes images of silver stained gel showing silver staining for *Strongylus vulgaris* (Lane A) larval and (Lane B) adult excretory/secretory (ES) fractions where low range molecular markers are shown to the left, and where Western blots are shown for (Lane C) reactivity of pre-immunisation rat serum against larval ES, (Lane D) reactivity of anti-adult *S. vulgaris* ES probed against larval ES, (Lane E) anti-adult *S. vulgaris* ES probed against adult ES, and (Lane F) reactivity of anti-adult *S. vulgaris* ES against larval ES where low range molecular markers are shown to the right.

SEQ ID NO: 1 is an amino acid sequence encoding an embodiment of an isolated *Strongylus vulgaris* SXP (SvSXP) peptide.

SEQ ID NO: 2 is an amino acid sequence encoding an embodiment of an isolated *Cylicostephanus goldi* SXP partial homologue.

SEQ ID NO: 3 is an amino acid sequence encoding an embodiment of an isolated *Necator americanus* surface-associated antigen (Na-SAA).

SEQ ID NO: 4 is an amino acid sequence encoding an embodiment of an isolated *Ancylostoma caninum* immunodominant hypodermal antigen (Ac16).

SEQ ID NO: 5 is an amino acid sequence encoding an embodiment of an isolated *Ascaris suum* 14 kDa antigen (As14).

SEQ ID NO: 6 is an amino acid sequence encoding an embodiment of an isolated *Ascaris lumbricoides* antigen 1 (Ag1).

SEQ ID NO: 7 is an amino acid sequence encoding an embodiment of an isolated *Parascaris equorum* partial SEQ ID NO: 8 is an amino acid sequence encoding an embodiment of an isolated SvSXP epitope is selected from C-Ahx-FANAGSMTDAAI-amide (svar-1).

SEQ ID NO: 9 is an amino acid sequence encoding an embodiment of an isolated SvSXP epitope is selected from C-AFAAFEKEIQSAQAQ-amide (svar-2).

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes methods, purified antibodies, isolated polypeptides, and kits useful for the diagnosis of *Strongylus vulgaris*.

In some embodiments, a method of diagnosing a *Strongylus vulgaris* infection in a subject is provided. In specific embodiments the *Strongylus vulgaris* infection is diagnosed during a prepatent period. Exemplary methods of diagnosing *Strongylus vulgaris* include providing a biological sample from the subject; and contacting the sample with a polypeptide. In some embodiments, the polypeptide can be the polypeptide of SEQ ID NO: 1 and/or a fragment thereof. Exemplary fragments of the polypeptide of SEQ ID NO: 1 can include at least 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, or 115 amino acid residues. In some embodiments, the polypeptide includes an epitope of the polypeptide of SEQ ID NO: 1, wherein the epitope is selected from C-Ahx-FANAGSMTDAAI-amide (svar-1)(SEQ ID NO: 8) and/or C-AFAAFEKEIQSAQAQ-amide (svar-2)(SEQ ID NO: 9).

The terms "diagnosing" and "diagnosis" as used herein refer to methods by which the skilled artisan can estimate and even determine whether or not a subject is suffering from a given disease or condition. The term diagnose or the like is inclusive of "prognosis" or "prognosticating," which is an area of interest since it can be useful to know the relative risk associated with particular conditions in order to plan the most effective therapy. If an accurate prognosis can be made, appropriate therapy, and in some instances less severe therapy or more effective therapy, for the patient can be chosen. In some embodiments of the presently disclosed subject matter, a method includes identifying a subject as having a *Strongylus vulgaris* infection, including one during a prepatent period. The term diagnosis can include determining a 10%, 20%, 30%, 40%, 50%, 60%, 70%, 80%, 90%, or 100% likelihood that the subject is suffering from a given disease or condition (e.g., *Strongylus vulgaris* infection).

In some embodiments, the method also includes detecting antibodies in the sample that specifically bind the polypeptide. Any method known to one of ordinary skill in the art can be used for such detection. For example, in some embodiments, the detection is conducted using an enzyme-linked immunosorbent assay (ELISA). In some embodiments, the subject is diagnosed as being infected by migrating *S. vulgaris* larvae when antibodies that specifically bind the polypeptide are detected in the sample.

The term "subject," as used herein, is inclusive of animal subjects. Thus, veterinary uses are provided in accordance with the presently disclosed subject matter and the presently-disclosed subject matter provides methods for preventing oxidative damage in animals. In specific embodiments the subject is a member of the Equidae taxonomic family. In some embodiments, the subject is a member of the *Equus* genus, including, for example, donkeys, mules, zebras, domesticated horses, *przewalski*, etc. In some embodiments, the subject can be a horse, including, for example, *Equus ferus*, and including subspecies *Equus ferus caballus* and *Equus ferus przewalskii*.

Furthermore, the biological sample can be any sample of biological tissue, cells, or fluids obtained from the subject. Exemplary samples include a blood sample from a subject. Another exemplary sample includes a serum sample from a subject. Further exemplary samples can include other biological fluids, such as peritoneal fluid or cerebrospinal fluid.

In some embodiments of the presently-disclosed subject matter, a method of diagnosing a *Strongylus vulgaris* infection in a subject during a prepatent period is provided and involves providing a biological sample from the subject; and contacting the sample with a purified antibody that specifically binds to an epitope of the polypeptide of SEQ ID NO: 1. In some embodiments, the epitope comprises the amino acid residues of SEQ ID NO: 1 selected from C-Ahx-FANAGSMTDAAI-amide (svar-1)(SEQ ID NO: 8) and/or C-AFAAFEKEIQSAQAQ-amide (svar-2)(SEQ ID NO: 9). In some embodiments, the method also involves detecting a polypeptide in the sample to which the antibody specifically binds. Any method known to one of ordinary skill in the art can be used for such detection. For example, in some embodiments, the detection is conducted using an enzyme-linked immunosorbent assay (ELISA). In some embodiments, the subject is diagnosed as being infected by migrating *S. vulgaris* larvae when the polypeptide to which the antibody specifically binds is detected in the sample. It is contemplated that in some embodiments of the method, the biological sample is a blood or a serum sample.

The presently-disclosed subject matter further includes an isolated polypeptide molecule, comprising the sequence of SEQ ID NO: 1 or a fragment thereof. Such fragment can include, for example, at least 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, or 115 amino acid residues of SEQ ID NO: 1. The fragment of the isolated peptide can comprise amino acids that have been removed from the carboxy-terminus, the amino-terminus, or both terminuses of the isolated polypeptide of SEQ ID NO: 1. In some embodiments the isolated peptide further comprises on or more amino acid substitutions, and is therefore a variant of the isolated polypeptide of SEQ ID NO: 1. The presently-disclosed subject matter further includes an isolated polypeptide molecule, comprising one or more epitopes of SEQ ID NO: 1 selected from C-Ahx-FANAGSMTDAAI-amide (svar-1)(SEQ ID NO: 8), and C-AFAAFEKEIQSAQAQ-amide (svar-2)(SEQ ID NO: 9). Such isolated polypeptide molecules can be made using techniques known to one of ordinary skill in the art, e.g., various molecular biological techniques for producing recombinant polypeptide molecules.

The terms "polypeptide", "protein", and "peptide", which are used interchangeably herein, refer to a polymer of the protein amino acids, or amino acid analogs, regardless of its size or function. The term "polypeptide" as used herein refers to peptides, polypeptides, and proteins, unless otherwise noted. The terms "protein", "polypeptide", and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The term "isolated", when used in the context of an isolated nucleotide or an isolated polypeptide, is a nucleotide or polypeptide that, by the hand of man, exists apart from its native environment and is therefore not a product of nature. An isolated nucleotide or polypeptide can exist in a purified form or can exist in a non-native environment such as, for example, in a transgenic host cell.

The presently-disclosed subject matter further includes a purified antibody that specifically binds a polypeptide molecule as disclosed herein. In some embodiments, the purified antibody specifically binds an epitope of the polypeptide of SEQ ID NO: 1. In specific embodiments the epitope of the polypeptide of SEQ ID NO: 1 comprises the amino acid residues of SEQ ID NO: 1 selected from C-Ahx-FANAGSMTDAAI-amide (svar-1)(SEQ ID NO: 8) and/or C-AFAAFEKEIQSAQAQ-amide (svar-2)(SEQ ID NO: 9). In some embodiments, the antibody is a monoclonal antibody.

The presently-disclosed subject matter further includes kits. Such kits can include a polypeptide comprising the polypeptide of SEQ ID NO: 1 and/or a fragment thereof comprising at least 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, or 115 amino acid residues; or a polypeptide comprising an epitope of the polypeptide of SEQ ID NO: 1, wherein the epitope is selected from C-Ahx-FANAGSMTDAAI-amide (svar-1) (SEQ ID NO: 8) and/or C-AFAAFEKEIQSAQAQ-amide (svar-2)(SEQ ID NO: 9). The kit can further comprise a substrate configured to receive a biological sample from a subject. In some embodiments, the polypeptide can be immobilized on a substrate. In some embodiments, the kit further includes reagents useful for detecting a binding between the polypeptide and an antibody in a biological sample.

In some embodiments, a kit can include an antibody that specifically binds an epitope of the polypeptide of SEQ ID NO: 1, wherein the epitope comprises the amino acid residues of SEQ ID NO: 1 selected from: C-Ahx-FANAGSMTDAAI-amide (svar-1)(SEQ ID NO: 8) and/or C-AFAAFEKEIQSAQAQ-amide (svar-2)(SEQ ID NO: 9). The kit can further comprise a substrate configured to receive a biological sample from a subject. In some embodiments, the antibody can be immobilized on a substrate. In some embodiments, the kit further includes reagents useful for detecting a binding between the antibody and a polypeptide in a biological sample.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a polypeptide" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting example. The following example may include compilations of data that are representative of data gathered at various times during the course of development and experimentation related to the present invention.

EXAMPLE

This Example employed immunoscreening of a *S. vulgaris* larval cDNA library to identify genes that encode stage-specific antigens. This Example also used these in immunodiagnostic assays for a prepatent diagnosis of *S. vulgaris*.

Materials and Methods

Horses

A total of 102 horses with necropsy-confirmed status of *S. vulgaris* infection were enrolled in the validation study. All necropsies were performed at either University of Kentucky in Lexington, Ky. or East Tennessee Clinical Research (ETCR) in Rockwood, Tenn.

All horses from University of Kentucky were naturally infected with mixed species of gastrointestinal helminth infections (n=31). They were enrolled from two main populations; a herd kept without anthelmintic intervention since 1979, and a population of research horses maintained with four anthelmintic treatments a year. Naturally infected horses from Tennessee (n=23) participated in different anthelmintic drug trials at ETCR and all underwent necropsy. In total, samples from 54 naturally infected horses were collected.

Experimental infections were carried out for two different research projects with horses maintained at ECTR (n=48). Horses in group P (n=20) were treated once daily for five consecutive days with fenbendazole paste (10 mg/kg, Panacur, Merck, Summit, N.J.), housed in stables and inoculated on a single occasion with 600 embryonated *P. equorum* eggs obtained locally from naturally infected horses. After six months the horses were euthanatised and necropsied. Horses in group S (n=28) were acquired with unknown anthelmintic treatment history, and were therefore treated with a larvicidal regimen of moxidectin (0.4 µg/kg, Quest gel, Pfizer, Madison, N.J.) administered once, and fenbendazole paste (10 mg/kg, Panacur) once daily for five consecutive days during the week prior to enrolment. They were subsequently infected with 5,000 cyathostomin third stage larvae ($L_3$) five times weekly throughout the study. Five weeks into the study the horses started receiving 25 *S. vulgaris* $L_3$ larvae once weekly until euthanasia and necropsy after 5.5 months.

At necropsy, the posterior aorta and cranial mesenteric artery and branches were recovered and evaluated for the presence of migrating *S. vulgaris* larvae in all horses.

The case-definition that served as the standard for classification of *S. vulgaris* positive horses was: horses with migratory tracts, one or more larvae, or evidence of previous infection. Migratory tracts were considered evidence of a current infection, and a circular area with raised surface, roughened or corrugated intima without evidence of active thrombosis was classified as evidence of previous infection. Horses with no migratory tracts, no larvae, and no signs of previous infection were classified as being *S. vulgaris*-negative.

The gastrointestinal and migrating parasites were enumerated as previously described.

A peripheral blood sample was collected from each horse (n=102) in a serum or serum-separator tube. Sera were separated by centrifugation, and duplicate aliquots were transferred to 2 mL cryovials and stored at −20° C. until analysis. The serum was stored for up to 5 years prior to analysis.

The horses in this study had a mean age of 19.5 months (range 0.6 months-22 years) with a median of 12 months of age. A total of 46 horses were female and 54 were males of which 12 were castrated. Data on age and gender was missing for two and one horse, respectively. The subset of horses 7 months and older had a mean age of 22.51 months (range 7 months-22 years) with a median of 18 months of age with 44 female, 42 males of which 12 were castrated. Data from horses 3 months and younger were omitted; the next youngest foal was 7 months old. Breeds represented included: Tennessee Walking Horse, Paint, American Quarter Horse, Thoroughbred, Standardbred, Appaloosa, Shetland type ponies and mixed light breed.

Parasite Material

Migrating *S. vulgaris* larvae were collected by dissection of the abdominal aorta, celiac artery, cranial mesenteric artery and major branches recovered from horses at the University of Kentucky that were naturally infected with gastrointestinal parasites and where anthelmintic drugs have not been used since 1979. The larvae were carefully lifted from the thrombus material and washed four times in 20 mL PBS (137 mM NaCl, 10 mM phosphate, 2.7 mM KCl, pH 7.4) to remove debris. The larvae were either placed in 2 mL cryotubes and snap frozen in liquid $N_2$ for RNA extraction or used for collection of ES antigens.

Worms were collected from the caeca of horses using the necropsy technique previously described, adult *S. vulgaris* worms were identified by morphological criteria and washed five times in 20 mL PBS to remove debris and used for collection of ES antigens.

Excretory/Secretory Antigens

Living washed adult worms were incubated in 5 mL RPMI-1640 (Life Technologies, Grand Island, N.Y.) with penicillin (100 IU/mL), streptomycin (100 IU/mL), amphotericin B (0.25 µg/mL) and a protease inhibitor cocktail (Protease inhibitor cocktail, P2714, Sigma-Aldrich, St. Louis, Mo.) in a 5% $CO_2$ incubator at 37° C. The medium was collected after 12 and 24 h and fresh medium was added. The protein concentration was analysed using the Bradford Protein quantitation assay (Pierce, Rockford, Ill.) as per the manufacturer's protocol. The ES antigen-rich medium was then dialysed against PBS at 4° C. using a 3 mL 3.5 kDa molecular cut-off Slide-A-Lyzer® (Pierce, Rockford, Ill.) according to the manufacturer's protocol. Dialysed ES antigen was frozen and shipped to Cocalico Biologicals, Inc. (Reamstown, Pa.) for production of hyperimmune serum. One rat was immunised with 250 µg adult *S. vulgaris* ES antigen mixed with Titermax® as adjuvant and given as six inoculations over a 61-day period. Due to background reactivity against *E. coli* proteins, the hyperimmune rat serum was pre-absorbed extensively against *E. coli* XL1-BLUE lysates.

Larval ES antigens were obtained from *S. vulgaris* larvae using 2 mL of RPMI-1640 (Life Technologies, Grand Island, N.Y.) with penicillin (100 IU/mL), streptomycin (100 IU/mL), amphotericin B (0.25 µg/mL) and a protease inhibitor cocktail (Protease inhibitor cocktail, P2714, Sigma-Aldrich, St. Louis, Mo.) and incubating the larvae in a 5% $CO_2$ incubator at 37° C. The medium was collected after 14 days during which time the dead larvae were removed daily with a sterile needle.

A total of 300 ng of *S. vulgaris* larval ES antigens was adjusted to 15 µL with water and mixed with 3 µL 5× sodium dodecyl sulphate-polyacrylamide gel electrophoresis (SDS-PAGE) sample buffer containing protease inhibitor cocktail. The same amount of *S. vulgaris* adult ES was prepared similarly. The ES mixtures were denatured at 95° C. for 5 min, placed on ice for 5 min and resolved in individual wells under reducing conditions in a 12% polyacrylamide gel, where after the gel was stained by silver staining Construction and Immunoscreening of Larval *S. vulgaris* cDNA Library RNA was extracted from $N_2$ frozen *S. vulgaris* larvae using the Trizol reagent (Life Technologies, Grand Island, N.Y.) and poly(A)+RNA (mRNA) was purified from total RNA using the NucleoTrap® mRNA-kit (Clontech, Mountain View, Calif.) according to the manufacturer's protocol. A total of 400 ng purified mRNA was used as template to synthesise cDNA using the SMART cDNA library construction kit (Clontech, Mountain View, Calif.), cloned into bacteriophage TriplEx2 lambda vector digested with NdeI and packaged using the Giga Pack III gold packaging extract (Agilent Technologies, Stratagene products division, La Jolla, Calif.) as previously described for a larval cyathostomin cDNA library. The titre of the cDNA library was evaluated and the quality was assessed by analysing cDNA inserts in 30 randomly-picked plaques by PCR analysis. The PCR products were cleaned using the Wizard® SV Gel and PCR clean-up system (Promega, Madison, Wis.) and sequenced at the University of Kentucky (Lexington, Ky.).

The *S. vulgaris* larval cDNA library was immunoscreened as described by the manufacturer (Clontech, Mountain View, Calif.). The primary immunoscreening was conducted on 100,000 cDNA clones. Plaque lifts were made onto nitrocellulose membranes (Fisher Scientific, Pittsburgh, Pa.) and the membranes were washed five times for 5 min in 25 mL TBST (100 mM Tris, 0.15 M NaCl and 0.05% Tween-20) and kept in TBST overnight at 4° C. The membranes were blocked with TBST+1% gelatine for 1 h at room temperature (RT) and probed with preabsorbed hyperimmune rat serum at 1:100 in TBST after washing. As secondary antibodies, horseradish peroxidase (HRP)-conjugated goat anti-rat IgG (H+L) (Jackson ImmunoResearch, Inc. West Grove, Pa.) were used at 1:10,000 in TBST after washing. The signal was developed using a chromogenic substrate (TMB stabilised substrate for HRP, Promega, Madison, Wis.) after washing. The membranes were aligned with the agar plate, and the positive clones were picked using p200 pipette tips. The selected plaque was placed in 500 µL Lambda dilution buffer (0.1 M NaCl, 10 mM $MgSO_4$, 3.5 mM Tris and 0.01% gelatin), vortexed for 30 s and kept at 4° C. The positive clones underwent secondary immunoscreening with the hyperimmune rat serum and rat-pre-immunisation serum as negative control to exclude false positive clones.

Sequence Analyses

Clones isolated from the cDNA library were amplified by PCR using vector-specific primers and sequenced at the University of Kentucky's Advanced Genetic Technology Center. The resulting sequences were used as queries in BLASTN searches against non-human, non-mouse nucleotide sequences and BLASTX searches against the non-redundant protein database from NCBI. The presence of a signal peptide was predicted using SignalP 4.0, the presence of glycosylation sites were analysed using the ExPASy Prosite, and the presence of transmembrane domains and protein localisation were predicted using TMHMM 2.0 server. Pairwise alignment and phylogenetic comparison was performed using the ClustalOmega software on the EBI-server. Homologues from *Cylicostephanus goldi* (University of Liverpool) and *P. equorum* (University of Berlin) were obtained and the partial sequences compared by pairwise alignment using the ClustalOmega software.

Expression of Recombinant Protein

Primers were designed to amplify the coding sequence from an immune-reactive cDNA clone for subcloning into a pET22b(+) vector. The primer sequences were as follows: Forward: 5'-GATCCATATGCAAAATGGACCTCCACC-3' and reverse: 5'-GATCCTCGAGTCCCTTCATAGCGTCC-3' which incorporated the NdeI and XhoI restriction sites (CATATG and CTCGAG) to allow for unidirectional cloning. The PCR was performed using Verbatim High Fidelity Polymerase (Thermo Fisher Scientific, Pittsburgh, Pa.) and the amplified fragment was digested with NdeI and XhoI and ligated with the pET22b(+) plasmid. The resulting plasmid was transformed into *E. coli* BL21 cells and expression of the recombinant protein was induced by 1 mM isopropyl-β-D-thiogalactopyranoside (IPTG) at an $OD_{600nm}$ of 0.6 and the cells were incubated under agitation for 9 h at 30° C. The recombinant protein was purified on immobilised cobalt by affinity chromatography using BD TALON resin (Clontech, Mountain View, Calif.) as per the manufacturer's protocol for soluble proteins. Purified recombinant protein was stored in aliquots at −20° C.

Hyperimmune Serum Against Recombinant Protein

A total of 300 µg of recombinant protein was resolved in 12% polyacrylamide gels under reducing conditions, a strip of the gel was stained with GelCode Blue stain (Thermo Scientific, Pittsburgh, Pa.) to verify where the recombinant antigen travelled in the gel and the corresponding part of the gel containing the desired molecular size was cut out and shipped to Cocalico Biologicals, Inc. (Reamstown, Pa.) and used to immunise a guinea pig with Freund's complete adjuvant for initial immunisation and Freund's incomplete adjuvant for subsequent boosters. The guinea pig was immunised by 6 inoculations of recombinant antigen over a period of 17 weeks.

Western Blot Analyses

*S. vulgaris* ES

For Western blot (WB) analysis of anti-adult *S. vulgaris* ES rat serum against both *S. vulgaris* larval and adult ES antigens were mixed with SDS-PAGE sample buffer containing protein inhibitor cocktail under reducing conditions and resolved in two 1-well 12% polyacrylamide gels. The proteins were transferred to 0.45 µm nitrocellulose membranes by semidry electrophoretic transfer in Tris-glycine buffer. Membranes were blocked for 1 h in PBST (PBS+0.05% Tween-20), and probed with pre-immunisation rat serum at 1:100 in PBST or hyperimmune rat serum raised against *S. vulgaris* adult ES at 1:100 in PBST. The signal was developed using TMB stabilised substrate for HRP (Promega, Madison, Wis.).

For WB analysis of anti-recombinant protein guinea pig serum against larval ES, 4.4 µg *S. vulgaris* larval ES was resolved in a 1-well 12% polyacrylamide gels, transferred to a nitrocellulose membrane and blocked. The nitrocellulose membrane was cut and strips were placed in individual trays. The strips were probed with either 500 µL of guinea pig pre-immunisation serum at 1:500 in PBST or guinea pig hyperimmune serum anti-recombinant protein at 1:2,500 in PBST. HRP-conjugated goat anti-horse IgG(T) (Bethyl Laboratories, Inc., Montgomery, Tex., USA), were used as secondary antibodies at 1:10,000 in PBST. The signal was developed using Supersignal WestPico chemiluminescent substrate (Pierce, Rockford, Ill.).

Recombinant Protein

Recombinant protein (233 ng) was resolved in each two 1-well 12% polyacrylamide gels by SDS-PAGE under reducing conditions and transferred to nitrocellulose membranes. The membranes were blocked and one was placed in a multi-slot apparatus (Bio Rad, Hercules, Calif.). The blot was probed with 500 µL horse serum samples (1:50 in PBST) in each slot. As secondary antibodies, HRP-conjugated goat anti-horse IgG(T) (Bethyl Laboratories, Inc., Montgomery, Tex.), were used at 1:10,000 in PBST. The signal was developed using Supersignal WestPico chemiluminescent substrate.

Strips were cut from the other blocked blot and placed in individual trays. The strips were probed with either pre-immunisation guinea pig serum at 1:500 in PBST or anti-recombinant protein guinea pig serum at 1:2500 in PBST. As secondary antibody, HRP-conjugated donkey anti-guinea pig IgG (H+L) (Jackson ImmunoResearch, Inc., West Grove, Pa.) were used at 1:10,000 in PBST. The signal was developed using Supersignal WestPico chemiluminescent substrate.

ELISA

The indirect ELISA was optimised by sequential checkerboard titration to the following setup. Individual wells of a 96 well EIA/RIA plate (Costar® easy-wash, Corning Inc., Corning, N.Y.) were coated with 75 µL of recombinant protein diluted to 0.1 µg/mL in PBS and incubated overnight at 4° C. The wells were washed three times for 1 min with PBST and blocked for 1½ h at RT with 200 µL block solution (PBS containing 5% normal goat serum, 1% dry milk powder and 1% Tween-20). The wells were washed once and 75 µL of horse serum diluted 1:50 in diluent solution (block solution in PBST, 1:10) was added to individual wells in duplicates and incubated for 1 h at 37° C. Positive, negative and blank controls were included on each plate in duplicates. The wells were washed five times with PBST, and 75 µL of HRP-conjugated goat anti-horse IgG (H+L) (Jackson ImmunoResearch, Inc. West Grove, Pa.) diluted 1:10,000 was added to each well and incubated for 1 h at 37° C. The wells were washed five times with PBST and incubated for 10 min at RT in the dark with 75 µL of RT 1-step Ultra TMB ELISA substrate (Thermo Scientific, Rockford, Ill.) per well. The reactions were stopped with 75 µL 2M $H_2SO_4$ per well, and the $OD_{450nm}$ determined using an E-max Precision Microplate Reader (Molecular Devices, Sunnyvale, Calif.) with a photometric range of 0.000 to 4.000 OD and a resolution of 0.001 OD.

IgG Subclass Antibodies

For evaluation of the optimal diagnostic antibody target in serum from 15 horses with known *S. vulgaris* larval infection status the level of antigen specific IgG subclasses IgGa, IgGb, IgGc and IgG(T) were evaluated using HRP-conjugated goat anti-horse IgGa, IgGb, IgGc and IgG(T) antibodies (Bethyl Laboratories, Inc., Montgomery, Tex.) at 1:40,000 as secondary antibodies as per the manufacturer's recommendation alongside the HRP-conjugated goat anti-horse IgG (H+L) secondary antibody as described in the ELISA setup.

After identifying the best antibody target, the secondary antibody dilution for the ELISA was optimised by checkerboard titration.

Diagnostic Accuracy of ELISA

These ELISAs were performed in June and July, 2012. Serum samples from all horses (n=102) and horses seven months and older (n=86) were evaluated for the level of antigen specific IgG and IgG(T) antibodies using the optimised ELISA in separate assays. The intra-assay variability of the ELISA was calculated from duplicate measurements from all horses. The inter-assay variability was calculated from the positive and negative controls included in each assay as well as specifically for three horses that were selected on the basis of their rSvSXP-specific IgG(T) $OD_{450nm}$. (OD value given in parentheses). These animals served as a high positive (2.708), an intermediate positive (1.278) and a negative (0.022). From each sample, a volume of 1,000 µL of serum diluted 1:50 in diluent solution was prepared to test triplicate samples on each of four sequential days to evaluate inter-assay variability as a normalised value, percentage of a positive control (PP), as previously described.

Statistical Analyses

The statistical program R, version 2.12 was used to generate graphs and perform statistical analyses. For all statistical analyses, a P-value less than or equal to 0.05 was considered significant.

Evaluation of IgG Subclasses

The non-parametric Wilcoxon rank sum test was used to compare IgG levels within each IgG subclass between *S. vulgaris* infected and uninfected horses.

Intra- and Inter-Assay Variability

The intra- and inter-assay % coefficient of variability (% CV) was calculated for each series of assays for each of the secondary antibodies. An intra-assay % CV below 10% and an inter-assay % CV below 20% were considered acceptable.

Receiver Operator Characteristics (ROC) Curve Analysis

ROC curve analyses were performed using the software package Epi for R for two sets of horses: all horses (n=102) and horses seven months or older (n=86). The reason for excluding foals in the second analysis was due to observations of high larval counts and corresponding low PP-values in some of the younger foals. After excluding horses younger than three months of age the remaining horses were all seven months or older. The cut-off was determined on the basis of the ROC curve analysis.

Diagnostic Accuracy

For the two sets of horses: all horses and horses 7 months and older the software package EpiR for R was used to calculate the diagnostic accuracy values; sensitivity, specificity, odds ratio, positive likelihood ratio (LR), and negative LR with corresponding 95% confidence intervals.

Correlation of Arterial *S. vulgaris* Larvae and rSvSXP-Specific Antibodies

The correlation between the number of *S. vulgaris* larvae in the cranial mesenteric artery and branches and the level of rSvSXP specific IgG(T)-antibodies expressed as the normalised PP-value was evaluated by the Spearman correlation test from the software package fBasics for R.

All horses (n=102) were categorised by the number of larvae present in the CMA and branches in the following five groups: Group 0: No larvae, migratory tracts or evidence of previous infection (n=42); group 1: No larvae, but migratory tracts or evidence of previous infection (n=16); group 2: 1-5 larvae (n=16); group 3: 6-25 larvae (n=17); and group 4: above 25 larvae (range: 25-292) (n=11).

A subset of the horses, horses 7 months or older (n=86), were categorised by the number of *S. vulgaris* larvae in the CMA and branches in the following five groups: Group 0: No larvae, migratory tracts or evidence of previous infection (n=28); group 1: Migratory tracts or evidence of previous infection (n=16); group 2: 1-5 larvae (n=16); group 3: 6-25 larvae (n=17); and group 4: above 25 larvae (range: 25-200) (n=9).

The relationship between the different groups and the PP values was evaluated graphically for both sets of horses. A Kruskal-Wallis test was performed to evaluate if there was a significant difference between groups and a multiple comparison test after Kruskal-Wallis performed to identify the significantly different groups using the statistical software package pgirmess for R. This was performed on both sets of horses.

Results

Preliminary Characterization of ES and Rat Anti-ES Serum

The silver staining of the polyacrylamide gel showed a diverse mixture of molecules in both *S. vulgaris* larval and adult ES (FIG. 1). The hyperimmune rat serum that was raised against *S. vulgaris* adult ES recognized more molecules in the adult ES than it did in the larval ES (FIG. 1).

cDNA Library and Immunoscreening

Titre analysis indicated that the primary unamplified cDNA library contained $4.75 \times 10^6$ plaque forming units (pfu)/mL. Thirty plaques were randomly selected from the library, and PCR analysis showed that 28 of the clones had inserts (93.3%) and that 26 of the 28 (92.9%) had inserts larger than or equal to 500 bp. Based on BLASTx searches, sequence analysis of the 26 large-insert clones from the quality assessment indicated that they all coded for different gene products. Horse serum from naturally infected horses was initially used for immunoscreening of the cDNA library; however, strong levels of anti-*E. coli* antibodies in the horse serum resulted in high background staining that could not be controlled.

Figure 2:
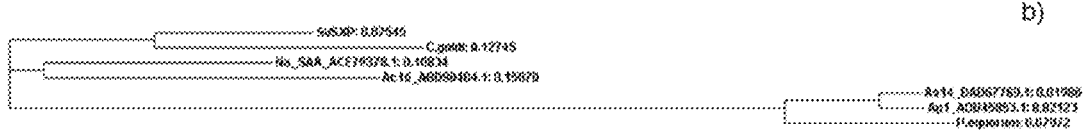
FIG. 2 includes A) ClustalOmega pairwise alignment of *Strongylus vulgaris* SXP (SvSXP) (SEQ ID NO: 1) (accession number: KC155360) with *Cylicostephanus goldi* SXP partial homologue (SEQ ID NO: 2), *Necator americanus* surface-associated antigen (Na-SAA) (ACE79378.1) (SEQ ID NO: 3), *Ancylostoma caninum* immunodominant hypodermal antigen (Ac16) (ABD98404.1) (SEQ ID NO: 4), *Ascaris suum* 14 kDa antigen (As14) (BAB67769.1) (SEQ ID NO: 5), *Ascaris lumbricoides* antigen 1 (Ag1) (ADB45853.1) (SEQ ID NO: 6), and *Parascaris equorum* partial homologue (SEQ ID NO: 7), where the signal peptide for each sequence is underlined and the domain of unknown function (DUF148) is boxed, asterisks (*) denote identical amino acids, double dots (:) denote conserved amino acid changes, a single dot (.) denotes semi-conserved amino acid changes, hyphen (-) indicates that a space was inserted in the sequence to improve alignment, and the percent similarity to SvSxP is listed for each homologous protein, and includes B) a phylogenetic tree of the above mentioned sequences.

The primary immunoscreening of 100,000 clones in the unamplified larval *S. vulgaris* cDNA library yielded 28 positive clones, all of which confirmed positive on secondary immunoscreening. The PCR products of these were all of comparable size (~650-680 bp) and sequence results of eight slightly different sized clones confirmed that their cDNAs coded for the same protein. The sequence encodes 146 amino acids including a predicted signal peptide (18 amino acids), giving rise to a mature peptide of 128 amino acids with an estimated molecular weight of 13.57 kDa. No glycosylation sites were predicted and the protein did not have any predicted transmembrane domains. The predicted translation showed that the encoded protein is homologous to the SXP/RAL-2 group of nematode specific proteins that contain a conserved Serine-X-Proline motif giving rise to the name. The protein was designated SvSXP. One sequence represented a full-length cDNA coding sequence, which was deposited [GenBank: KC155360]. SvSXP had highest amino acid sequence similarity with a partial sequence from the *Cylicostephanus goldi* homologue, followed by the surface-associated antigen 2 (SAA-2) from *Necator americanus* [Genbank: ACE79378.1], and thirdly the immunodominant-hypodermal antigen AC16 from *Ancylostoma caninum* [Genbank: ABD98404.1]. Two partial sequences from a *P. equorum* derived homologue had a lesser degree of similarity (35% and 46% identities) (FIG. 2A). The phylogenetic comparison clustered C. goldi with *S. vulgaris*, *P. equorum* with *Ascaris suum* and N. americanus with *A. caninum* (FIG. 2B).

Analysis of SvSXP in *S. vulgaris* Larval ES

Figure 3:
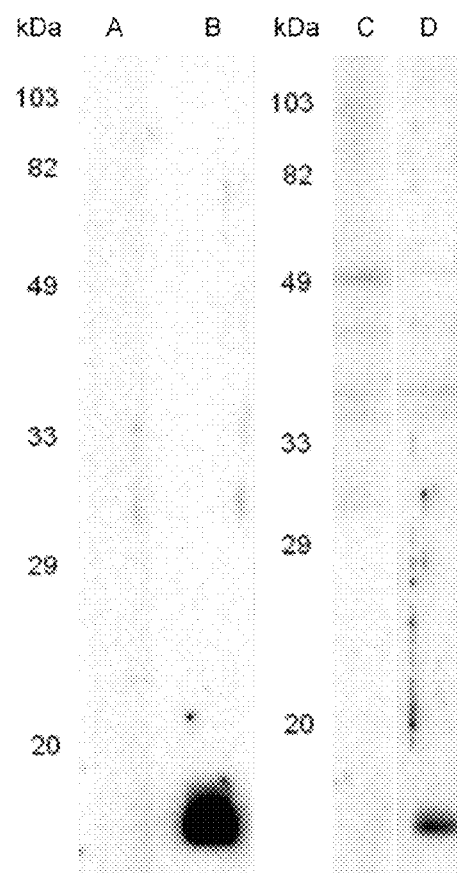
FIG. 3 includes a Western blot analysis of pre-immunisation guinea pig serum (Lanes A and C) and hyperimmune anti-rSvSXP guinea pig serum (Lanes B and D) against rSvSXP (Lanes A and B) and *Strongylus vulgaris* larval excretory/secretory antigens (Lanes C and D). The molecular weight markers are shown to the left of each type of antigen.

Western blot analyses of rSvSXP and larval ES using hyperimmune guinea pig anti-rSvSXP serum showed that the hyperimmune serum recognized a molecule of similar size in both blots. The pre-immunisation guinea pig serum did not react against the 14 kDa recombinant antigen (FIG. 3).

Figure 4:
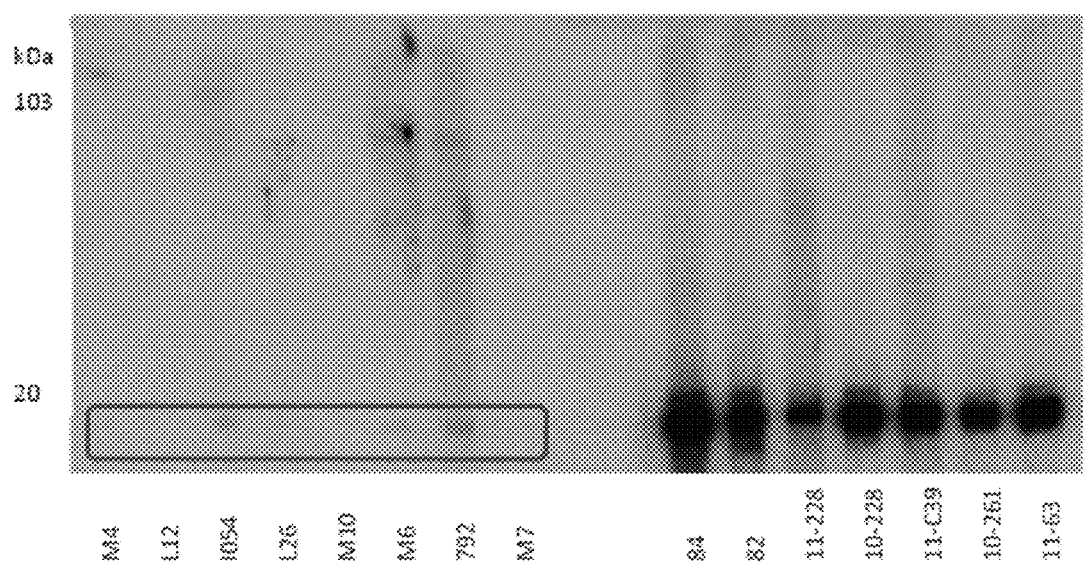
FIG. 4 includes Western blot showing 233 ng recombinant SvSXP (Lanes 1-8, box) probed with serum from *Strongylus vulgaris* negative horse and (Lanes 9-15) probed with serum from *S. vulgaris* positive horses. The molecular weight is indicated on the left size.

Western Blot Analyses of IgG Antibodies Against rSvSXP in *S. vulgaris*-Positive and Negative Horses The immunodiagnostic potential of antigen-specific IgG and IgG(T) antibodies against rSvSXP were evaluated by WB. These analyses revealed limited IgG reactivity to rSvSXP in serum from two horses not infected with *S. vulgaris* and low level IgG(T) reactivity to rSvSXP in serum from eight horses not infected with *S. vulgaris* (FIG. 4), as determined by post-mortem examination. In contrast, serum from seven horses infected with *S. vulgaris* showed a reaction to rSvSXP (FIG. 4).

Diagnostic Potential of IgG Subclass Antibodies

Figure 5:
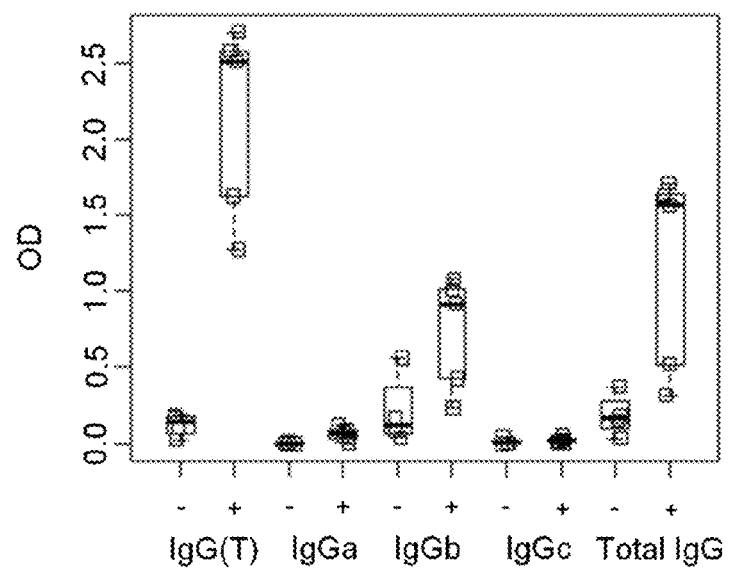
FIG. 5 includes a boxplot showing optic density readings of the enzyme-linked immunosorbent assay with antigen specific IgG subclasses grouped by *Strongylus vulgaris* infection status. −: no *S. vulgaris* larvae; +: *S. vulgaris* larvae present in the cranial mesenteric artery or branches. The middle black line of the box is the median and the range of the box is the inter quartile range (IQR) giving the first and third IQR. The lower and upper lines are up to 1.5 IQR away from the first and third quartile. Each square represents the mean $OD_{450nm}$ reading from one serum sample for each IgG subclass. Asterisks denote significant differences (p<0.05) between uninfected and infected horses within each IgG subclass.

Analysis of rSvSXP-specific IgG subclasses by ELISA showed that detection of rSvSXP-specific IgG(T) antibodies gave the clearest distinction between the seven *S. vulgaris* positive horses and the eight *S. vulgaris* negative horses, while the other IgG subclasses were less consistent (FIG. 5). Both the IgG subclasses IgGa (P=0.016) and IgG(T) (P=0.016) as well as total IgG (P=0.032) showed statistically significant differences between infected and non-infected horses (n=15).

Inter- and Intra-Assay Coefficients of Variability

The intra-assay variability of the ELISA measuring rSvSXP-specific IgG(T) antibodies was 9.17% for all the duplicate measurements. For the IgG(T) assays that were included, the inter-assay % CV for the positive control was 16.9% while the inter-assay % CV for the negative control was 72.6% resulting in an overall inter-assay % CV of 44.8%. When using the PP-value, the overall inter-assay % CV dropped to 15.6%. The overall inter-assay % CV for the IgG assays, all measured on the same day, was 11.8%.

Horse Material Used for Evaluation of Diagnostic Values of the ELISA

The prevalence of arterial lesions as well as the seroprevalence in each group of horses is shown in Table 1.

TABLE 1

Prevalence of *Strongylus vulgaris* expressed as prevalence of arterial lesions and seropositive horses. Sensitivity (Se) and specificity (Sp) is presented for each group of horses.

| Group of horses | Prevalence of arterial lesions | Seropositive prevalence | Se | Sp |
| --- | --- | --- | --- | --- |
| KY, naturally infected, never treated herd (n = 11) | 100% | 90.1% | 90.9% | 100% |
| KY, naturally infected, treated herd (n = 20) | 10% | 5% | 50% | 100% |
| TN, naturally infected (n = 23) | 73.9% | 87.0% | 94% | 33% |
| TN, experimentally infected with *P. equorum* (n = 20) | 70% | 50% | 64% | 83% |
| TN, experimentally infected with *S. vulgaris* and Cyathostomins (n = 28) | 57.1% | 39.3% | 50% | 75% |

Case definition: A *S. vulgaris* positive horse has presence of larvae, migratory tracts or healing lesions
Cut-off value used: seropositive: PP-value above 8.75.

A total of 42 horses showed no signs of migrating larvae in the CMA and branches or signs of previous infection and were classified as *S. vulgaris*-negative, larvae with migratory tracts and evidence of thrombosis were found in 47 horses, and migratory tracts or healing lesions were found in 19 horses, of these 10 were determined to show evidence of a previous infection.

Figure 6:
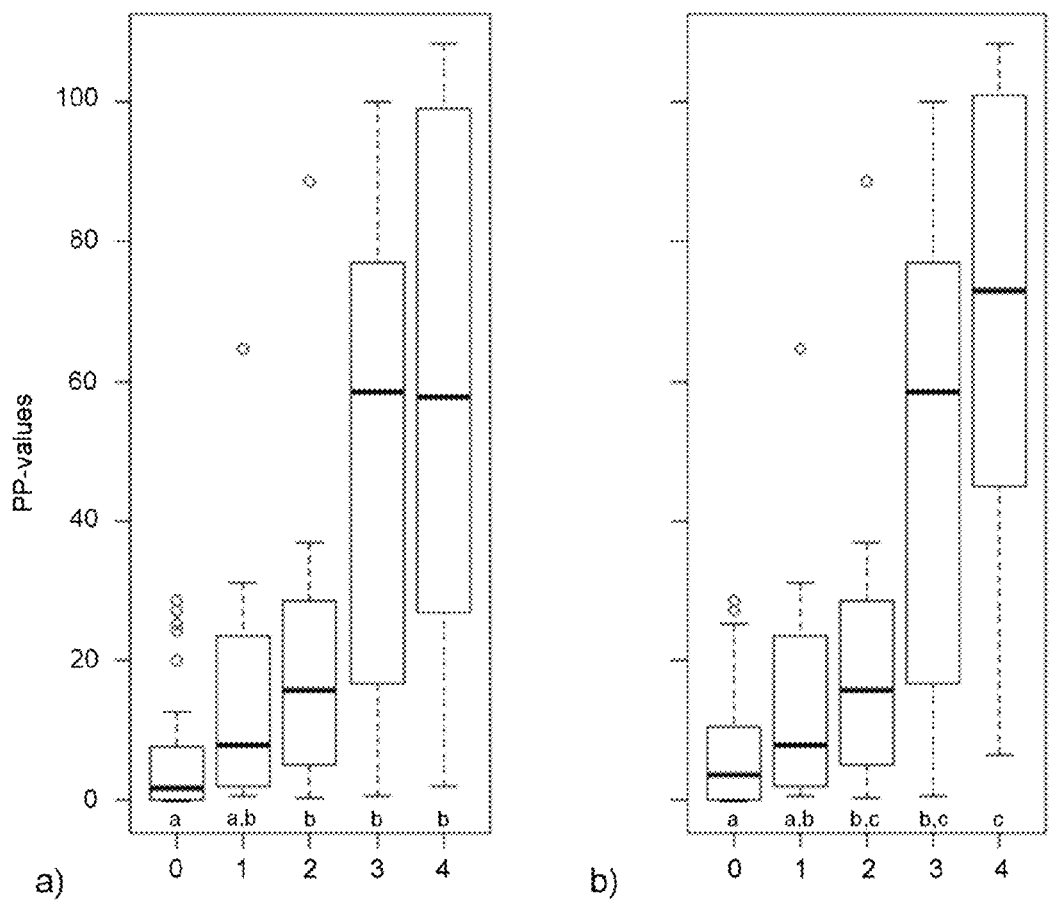
FIG. 6 includes graphs of the relationship between serum anti-rSvSXP IgG(T) antibody levels (expressed as percentage of a positive control) and counts of migrating *Strongylus vulgaris* larvae categorised by their number of larvae showing a) all 102 horses in the data set and b) the 86 horses in the data set aged 7 months and older. Group 0: No larvae, migratory tracts nor evidence of previous infection

In the subset of horses seven months or older, 29 were classified as *S. vulgaris*-negative with no sign of current or previous infection; 42 horses had migrating larvae, migratory tracts and evidence of thrombosis; 17 horses had migratory tracts or healing lesions but no larvae, of these seven were determined to show evidence of a previous infection. The relationship between numbers of migrating arterial *S. vulgaris* larvae and ELISA results is illustrated in FIG. 6. In the full dataset there was a significant difference in the level of anti-SvSXP IgG(T) antibodies, expressed as the PP-value, between *S. vulgaris*-negative horses (Group 0) and horses with migrating larvae (groups 2,3 and 4). In the subset of horses seven months and older there was a significant difference between the same groups as well as a significant difference between horses with no larvae but evidence of migratory tracts, aneurysm or healing lesions (group 1), and horses with a heavy infection (group 4).

A moderate positive correlation was found between the number of *S. vulgaris* larvae in the CMA and branches and the PP-value with an $R_s$ of 0.5779 (0.433-0.693), P<0.0001 in the data set including all horses. In the data set including horses 7 months and older there was a moderate positive correlation between the number of *S. vulgaris* larvae in the CMA and branches and the PP-value with an $R_s$ of 0.5944 (0.44-0.714), P<0.0001.

Diagnostic Accuracy

The relationship between sensitivity and specificity is listed for the two datasets at different cut-off values (Table 2).

TABLE 2

Sensitivity and specificity at different cut-off values of antibody responses against rSvSXP expressed as percent of a positive control (PP) for (A) all horses (n = 102) or (B) horses 7 months or older (n = 86).

| Data set | A | | B | |
|---|---|---|---|---|
| PP cut-off | Se$ | Sp$ | Se | Sp |
| 5 | 0.77 | 0.67 | 0.78 | 0.54 |
| 10 | 0.70 | 0.83 | 0.71 | 0.75 |
| 15 | 0.64 | 0.88 | 0.66 | 0.82 |
| 20 | 0.53 | 0.88 | 0.55 | 0.82 |
| 25 | 0.48 | 0.90 | 0.50 | 0.86 |
| 30 | 0.42 | 0.98 | 0.43 | 0.96 |
| 40 | 0.37 | 1 | 0.38 | 1 |
| 50 | 0.32 | 1 | 0.33 | 1 |
| 60 | 0.27 | 1 | 0.28 | 1 |
| 70 | 0.22 | 1 | 0.22 | 1 |
| 80 | 0.17 | 1 | 0.17 | 1 |
| 90 | 0.12 | 1 | 0.12 | 1 |
| 100 | 0.08 | 1 | 0.09 | 1 |
| >100 | 0.05 | 1 | 0.02 | 1 |
| AUC$ | 0.820 | | 0.783 | |

$: Se: sensitivity; Sp: specificity; AUC: area under ROC curve.

The diagnostic accuracy values expressed as sensitivity, specificity, diagnostic odds ratio, LR+ and LR− for each set of horses are shown for the optimal cut-off PP value in Table 3.

TABLE 3

Diagnostic accuracy values with 95% confidence intervals using the same cut-off value for (A) all horses (n = 102) or (B) horses 7 months or older (n = 86).

| Data set: | A | | B | |
|---|---|---|---|---|
| Cut-off value (PP) | 8.75 | | 13.47 | |
| Se | 73.3% | (60.3-83.9%) | 65.5% | (51.9-77.5%) |
| Sp | 81.0% | (65.9-91.4%) | 82.1% | (63.1-93.9%) |
| DOR | 11.69 | (4.48-30.5) | 8.74 | (2.89-26.48) |

TABLE 3-continued

Diagnostic accuracy values with 95% confidence intervals using the same cut-off value for (A) all horses (n = 102) or (B) horses 7 months or older (n = 86).

| Data set: | A | | B | |
|---|---|---|---|---|
| Cut-off value (PP) | 8.75 | | 13.47 | |
| LR+ | 3.85 | (2.03-7.32) | 3.67 | (1.62-8.30) |
| LR− | 0.33 | (0.21-0.51) | 0.42 | (0.28-0.62) |

Cut-off values represent optimal sensitivity and specificity for each case-definition. PP: percent of a positive control; Se: sensitivity; Sp: specificity; DOR: diagnostic odds ratio; LR+: positive likelihood ratio; LR−: negative likelihood ratio. The 95% confidence intervals are given in parentheses.

Accordingly, the present protein meets at least four criteria: (i) the recombinant protein was bound by serum IgG(T) primarily from horses harboring infection or exhibiting lesions associated with previous presence of *S. vulgaris* larvae; (ii) the diagnostic odds ratio of the ELISA showed that infection with migrating *S. vulgaris* larvae significantly increased the possibility of a positive test result; (iii) other naturally occurring equine gastrointestinal nematodes did not appear to interact with test results; (iv) there is evidence of a semi-quantitative relationship between infection intensity and ELISA results.

The data generated in this Example is from horses being either naturally or experimentally infected with major equine helminth parasites. The experimental infections with *P. equorum* and cyathostomin parasites did not appear to dramatically affect diagnostic performance (Table 1). Further, four out of five of the defined subpopulations returned higher sensitivity than specificity. It is considered useful to evaluate the diagnostic odds ratio (DOR) and the likelihood ratios (LR) that are presented in Table 3. The DORs were high and statistically significant, and the test is characterized by a strong positive LR. High levels of cross-reactivity with other species and stages would have led to more false-positive test results, and, thus, a lower positive LR. Taken together, rSvSXP represents a well-characterized and validated diagnostic antigen for *S. vulgaris* diagnosis.

As the hyperimmune rat serum was raised against adult *S. vulgaris* ES antigens and this was used to perform the immunoscreening of the *S. vulgaris* larval cDNA library, the protein is expressed in both larval and adult stages. Thus, it is possible that adult stages in the intestine are also capable of affecting ELISA measurements. IgG(T) antibodies in some animals does not differ from the non-specific background reactivity in controls, suggesting that the immune response and hence antibody production is primarily stimulated by the migrating larvae and not the adult worms. Therefore, it is possible that the presence of the larvae in the blood stream of the horse will allow a higher degree of exposure of the SXP protein to the immune system.

Here, IgG(T) antibodies specific to rSvSXP appeared to have a immunodiagnostic potential than other IgG subclasses (FIGS. 5 and 6). The intra-assay % CV of mean $OD_{450nm}$ values was within acceptable levels and the inter-assay % CV was higher. The use of the normalised PP value reduced the inter-assay % CV.

The semi-quantitative potential of the procedure is illustrated in FIG. 6. A separate analysis was performed in horses older than seven months to evaluate if the ELISA would perform better in this age group. FIGS. 6a and 6b seems to indicate that larval burden and the PP-value correlate more closely when foals were excluded. This illustrates that younger foals can harbor migrating larvae without producing antibody titres.

The ELISA performed with a sensitivity and specificity comparable to larval cultures carried out for detection of *S. vulgaris* eggs, and has potential for reflecting the number of arterial larvae. The odds of a PP-value above the cut-off among horses with migrating *S. vulgaris* larvae, migratory tracts or evidence of previous infection was 11.7 times higher than the odds of a similar ELISA result among horses without migrating *S. vulgaris* larvae or signs thereof. Moreover, a high PP-value indicates a high number of migrating larvae (FIG. 6).

Throughout this document, various references are mentioned. All such references are incorporated herein by reference, including the references set forth in the following list:

REFERENCES

Adeyefa, C. A. O., 1992. Precipitin response of the mitogen produced by *Strongylus vulgaris* arterial larvae. Vet. Parasitol. 43, 243-247.

Andersen U V, Howe D K, Olsen S N, Nielsen M K: Recent advances in diagnosing pathogenic equine gastrointestinal helminths: The challenge of prepatent detection. *Vet Parasitol* 2013, 192(1-3):1-9.

Balasuriya, U. B., Shi, P. Y., Wong, S. J., Demarest, V. L., Gardner, I. A., Hullinger, P. J., Ferraro, G. L., Boone, J. D., De Cino, C. L., Glaser, A. L., Renshaw, R. W., Ledizet, M., Koski, R. A., MacLachlan, N. J., 2006. Detection of antibodies to West Nile virus in equine sera using microsphere immunoassay. Journal of veterinary diagnostic investigation: official publication of the American Association of Veterinary Laboratory Diagnosticians, Inc 18, 392-395.

Bevilaqua, C. M. L., Rodrigues, M. L., Concordet, D., 1993. Identification of infective larvae of some common nematode strongylids of horses. Rev. Med. Vet.—Toulouse 12, 989-995.

Bjorn H, Sommer C, Schougard H, Henriksen S A, Nansen P: Resistance to benzimidazole anthelmintics in small strongyles (Cyathostominae) of horses in Denmark. *Acta Vet Scand* 1991, 32(2):253-260.

Bollinger, O. 1870. Die Kolik der Pferde and das Wurmaneurysma der Eingeweidearterien. In Müchener Sitzungsberichte Königliche Bayerischen Akademie der Wissenschaften, Mathematischnaturwissenchaftliche Abteilung 1, pp. 530-544.

Carstensen B, Plummer M, Laara E, Hills M: Epi: A Package for Statistical Analysis in Epidemiology. In., R package version 1.1.24. edn; 2011.

Chandrashekar, R., Curtis, K. C., Ramzy, R. M., Liftis, F., Li, B. W., Weil, G. J., 1994. Molecular cloning of *Brugia malayi* antigens for diagnosis of lymphatic filariasis. Mol. Biochem. Parasitol. 64, 261-271.

Cho, M. K., Lee, K. H., Lee, S. J., Kang, S. W., Ock, M. S., Hong, Y. C., Lee, Y. S., Yu, H. S., 2009. Identification of host immune regulation candidate genes of *Toxascaris leonina* by expression sequenced tags (ESTs) analysis. Vet. Parasitol. 164, 242-247.

20. Coles G C: Sustainable use of anthelmintics in grazing animals. *Vet Rec* 2002, 151(6):165-169.

Curtis, R. A., 1964. Mesenteric Aneurism in a Horse. Can Vet J 5, 36-38.

Davidson, A. J., Hodgkinson, J. E., Proudman, C. J., Matthews, J. B., 2005. Cytokine responses to Cyathostominae larvae in the equine large intestinal wall. Res. Vet. Sci. 78, 169-176.

Dissanayake, S., Xu, M., Piessens, W.F., 1992. A cloned antigen for serological diagnosis of *Wuchereria bancrofti* microfilaremia with daytime blood samples. Mol. Biochem. Parasitol. 56, 269-277.

Dowdall, S. M. J., Matthews, J. B., Mair, T., Murphy, D., Love, S., Proudman, C. J., 2002. Antigen-specific IgG(T) responses in natural and experimental cyathostominae infection in horses. Vet. Parasitol. 106, 225-242.

Drudge, J. H., Lyons, E. T., 1966. Control of internal parasites of the horse. J. Am. Vet. Med. Assoc. 148, 378-383.

Drudge, J. H., Lyons, E. T., Szanto, J., 1966. Pathogenesis of migrating stages of helminths, with special reference to *Strongylus vulgaris*. In: Proceedings of the world Association for the Advancement of Veterinary Parasitology, New York & London, pp. 199-214.

Drudge, J. H., Szanto, J., Wyant, Z. N., Elam, G., 1963. Critical Tests of Thiabendazole as an Anthelmintic in the Horse. Am. J. Vet. Res. 24, 1217-1222.

Duncan, J. L., Pirie, H. M., 1972. The life cycle of *Strongylus vulgaris* in the horse. Res. Vet. Sci. 13, 374-379.

Duncan, J. L., Pirie, H. M., 1975. The pathogenesis of single experimental infections with *Strongylus vulgaris* in foals. Res. Vet. Sci. 18, 82-93.

Enigk, K., 1970. The development of the three species of Strongylus of the horse during the prepatent period. In: Equine infectious diseases, Basel: S. Karger., pp. 259-268.

Fujiwara, R. T., Zhan, B., Mendez, S., Loukas, A., Bueno, L. L., Wang, Y., Plieskatt, J., Oksov, Y., Lustigman, S., Bottazzi, M. E., Hotez, P., Bethony, J. M., 2007. Reduction of worm fecundity and canine host blood loss mediates protection against hookworm infection elicited by vaccination with recombinant Ac-16. Clin. Vaccine Immunol. 14, 281-287.

Go, Y. Y., Wong, S. J., Branscum, A. J., Demarest, V. L., Shuck, K. M., Vickers, M. L., Zhang, J., McCollum, W. H., Timoney, P. J., Balasuriya, U. B., 2008. Development of a fluorescent-microsphere immunoassay for detection of antibodies specific to equine arteritis virus and comparison with the virus neutralization test. Clin. Vaccine Immunol. 15, 76-87.

Hassan, S. E., Ghazy, A. A., Abdel-Rahman, E. H., 2010. Isolation and characterization of immunodiagnostic antigen from *Strongylus vulgaris* infecting horses. World Appl. Sci. J. 8, 235-240.

Henderson, K., Stewart, J., 2000. A dipstick immunoassay to rapidly measure serum oestrone sulfate concentrations in horses. Reprod Fertil Dev 12, 183-189.

Herd, R. P., Willardson, K. L., Gabel, A. A., 1985. Epidemiological approach to the control of horse strongyles. Equine Vet. J. 17, 202-207.

Hooper-McGrevy, K. E., Wilkie, B. N., Prescott, J. F., 2003. Immunoglobulin G subisotype responses of pneumonic and healthy, exposed foals and adult horses to *Rhodococcus equi* virulence-associated proteins. Clin Diagn Lab Immunol 10, 345-351.

Höglund, J., Ljungstrom, B. L., Nilsson, O., Lundquist, H., Osterman, E., Uggla, A., 1997. Occurrence of *Gasterophilus intestinalis* and some parasitic nematodes of horses in Sweden. Acta Vet. Scand. 38, 157-165.

Kaplan, R. M., 2002. Anthelmintic resistance in nematodes of horses. Vet Res 33, 491-507.

Kaplan, R. M., 2004. Drug resistance in nematodes of veterinary importance: a status report. Trends. Parasitol. 20, 477-481.

Kaplan R M, Nielsen M K: An evidence-based approach to equine parasite control: It ain't the 60s anymore. *Equine Vet Educ* 2010, 22(6):306-316.

Klei, T. R., Chapman, M. R., Torbert, B. J., McClure, J. R., 1983. Antibody responses of ponies to initial and challenge infections of *Strongylus vulgaris*. Vet. Parasitol. 12, 187-198.

Knudsen T, Kjelgaard-Hansen M, Tranholm M, Wiinberg B, Clausen J T, Hansen J J, Nichols T C, Kjalke M, Jensen A L, Kristensen A T: Canine specific ELISA for coagulation factor VII. *Vet J* 2011, 190(3):352-358.

Lalitha, P., Eswaran, D., Gnanasekar, M., Rao, K. V., Narayanan, R. B., Scott, A., Nutman, T., Kaliraj, P., 2002. Development of antigen detection ELISA for the diagnosis of brugian and bancroftian filariasis using antibodies to recombinant filarial antigens Bm-SXP-1 and Wb-SXP-1. Microbiol Immunol 46, 327-332.

Lawson, S., Lunney, J., Zuckermann, F., Osorio, F., Nelson, E., Welbon, C., Clement, T., Fang, Y., Wong, S., Kulas, K., Christopher-Hennings, J., 2010. Development of an 8-plex Luminex assay to detect swine cytokines for vaccine development: assessment of immunity after porcine reproductive and respiratory syndrome virus (PRRSV) vaccination. Vaccine 28, 5356-5364.

Lichtenfels, J. R., Kharchenko, V. A., Dvojnos, G. M., 2008. Illustrated identification keys to strongylid parasites (Strongylidae: Nematoda) of horses, zebras and asses (Equidae). Vet. Parasitol. 156, 4-161.

Lyons, E. T., Tolliver, S. C., Stamper, S., Drudge, J. H., Granstrom, D. E., Collins, S. S., 1994. Transmission of some species of internal parasites in horses born in 1990, 1991, and 1992 in the same pasture on a farm in central Kentucky. Vet. Parasitol. 52, 257-269.

Lyons E T, Tolliver S C, Ionita M, Collins S S: Evaluation of parasiticidal activity of fenbendazole, ivermectin, oxibendazole, and pyrantel pamoate in horse foals with emphasis on ascarids (*Parascaris equorum*) in field studies on five farms in Central Kentucky in 2007. *Parasitol Res* 2008, 103(2):287-291.

McWilliam, H. E., Nisbet, A. J., Dowdall, S. M., Hodgkinson, J. E., Matthews, J. B., 2010. Identification and characterisation of an immunodiagnostic marker for cyathostomin developing stage larvae. Int. J. Parasitol. 40, 265-275.

Morgan, S. J., Stromberg, P. C., Storts, R. W., Sowa, B. A., Lay, J. C., 1991. Histology and Morphometry of *Strongylus vulgaris*-Mediated Equine Mesenteric Arteritis. J. Comp. Pathol. 104, 89-99.

Nichol, C., Masterson, W. J., 1987. Characterisation of surface antigens of *Strongylus vulgaris* of potential immunodiagnostic importance. Mol. Biochem. Parasitol. 25, 29-38.

Nielsen, M. K., Monrad, J., Olsen, S. N., 2006. Prescription-only anthelmintics—a questionnaire survey of strategies for surveillance and control of equine strongyles in Denmark. Vet. Parasitol. 135, 47-55.

Nielsen M K, Baptiste K E, Tolliver S C, Collins S S, Lyons E T: Analysis of multiyear studies in horses in Kentucky to ascertain whether counts of eggs and larvae per gram of feces are reliable indicators of numbers of strongyles and ascarids present. *Vet Parasitol* 2010, 174(1-2):77-84.

Nielsen M K, Vidyashankar A N, Olsen S N, Monrad J, Thamsborg S M: *Strongylus vulgaris* associated with usage of selective therapy on Danish horse farms—is it reemerging? *Vet Parasitol* 2012, 189(2-4):260-266.

Nielsen, M. K., Peterson, D. S., Monrad, J., Thamsborg, S. M., Olsen, S. N., Kaplan, R. M., 2008. Detection and semi-quantification of *Strongylus vulgaris* DNA in equine faeces by real-time quantitative PCR. Int. J. Parasitol. 38, 443-453.

Pandiaraja, P., Arunkumar, C., Hoti, S. L., Rao, D. N., Kaliraj, P., 2010. Evaluation of synthetic peptides of WbSXP-1 for the diagnosis of human lymphatic filariasis. Diagn Microbiol Infect Dis 68, 410-415.

Patton, S., Mock, R. E., Drudge, J. H., Morgan, D., 1978. Increase of immunoglobulin T concentration in ponies as a response to experimental infection with the nematode *Strongylus vulgaris*. Am. J. Vet. Res. 39, 19-23.

Petersen, T. N., Brunak, S., von Heijne, G., Nielsen, H., 2011. SignalP 4.0: discriminating signal peptides from transmembrane regions. Nat Methods 8, 785-786.

Pilo C, Altea A, Pirino S, Nicolussi P, Varcasia A, Genchi M, Scala A: *Strongylus vulgaris* (Looss, 1900) in horses in Italy: Is it still a problem? *Vet Parasitol* 2012, 184(2-4): 161-167.

Proudman, C. J., Trees, A. J., 1996. Correlation of antigen specific IgG and IgG(T) responses with *Anoplocephala perfoliata* infection intensity in the horse. Parasite Immunol. 18, 499-506.

Rao, K. V., Eswaran, M., Ravi, V., Gnanasekhar, B., Narayanan, R. B., Kaliraj, P., Jayaraman, K., Marson, A., Raghavan, N., Scott, A. L., 2000. The *Wuchereria bancrofti* orthologue of *Brugia malayi* SXP1 and the diagnosis of bancroftian filariasis. Mol. Biochem. Parasitol. 107, 71-80.

Reinemeyer C R, Prado J C, Schricker B, Kennedy T: Parasitologic, Physiologic, and Performance Parameters of Yearling Horses Receiving Daily Pyrantel Tartrate. In: *J Equine Vet Sci*. vol. 32; 2012: S40.

Round, M. C., 1969. The prepatent period of some horse nematodes determined by experimental infection. J. Helminthol. 43, 185-192.

Russell, A. F., 1948. The development of helminthiasis in thoroughbred foals. J. Comp. Pathol. 58, 107-127.

Sambrook, J., Russell, D. W., 2001. Removal of Cross-reactive Antibodies from Antiserum: Pseudoscreening, In: Molecular Cloning: A Laboratory Manual. Cold Harbor Spring Laboratory Press, Cold Spring Harbor, N.Y., p. 14.25.

Sasisekhar, B., Aparna, M., Augustin, D. J., Kaliraj, P., Kar, S. K., Nutman, T. B., Narayanan, R. B., 2005. Diminished Monocyte Function in Microfilaremic Patients with Lymphatic Filariasis and Its Relationship to Altered Lymphoproliferative Responses. Infect Immun 73, 3385-3393.

Schougaard H, Nielsen M K: Apparent ivermectin resistance of *Parascaris equorum* in foals in Denmark. *Vet Rec* 2007, 160(13):439-440.

Slocombe, J. O., McCraw, B. M., 1973. Gastrointestinal nematodes in horses in Ontario. Can Vet J 14, 101-105.

Slocombe J O, de Gannes R V, Lake M C: Macrocyclic lactone-resistant *Parascaris equorum* on stud farms in Canada and effectiveness of fenbendazole and pyrantel pamoate. *Vet Parasitol* 2007, 145(3-4):371-376.

Stevenson M, Nunes T, Sanchez J, Thornton R: epiR: Functions for analysing epidemiological data. In.; 2011.

Team RDC: R: A language and environment for statistical computing. In.; 2011.

Thompson R C A: Veterinary Parasitology: Looking to the Next Millenium. *Parasitol Today* 1999, 15(8):320-325.

TMHMM version 2.0 [http://www.cbs.dtu.dk/services/TM-HMM/]

Traversa D, von Samson-Himmelstjerna G, Demeler J, Milillo P, Schurmann S, Barnes H, Otranto D, Perrucci S, di Regalbono A F, Beraldo P et al: Anthelmintic resistance in cyathostomin populations from horse yards in Italy, United Kingdom and Germany. *Parasit Vectors* 2009, 2.

Tytgat, T., Vercauteren, I., Vanholme, B., De Meutter, J., Vanhoutte, I., Gheysen, G., Borgonie, G., Coomans, A., 2005. An SXP/RAL-2 protein produced by the subventral pharyngeal glands in the plant parasitic root-knot nematode *Meloidogyne incognita*. Parasitol. Res. 95, 50-54.

Van Wyk J A, Vanwijk E F: Resistance of Small Strongyles in an Equine Stud in South-Africa to the Benzimidazole Anthelmintics. *Journal of the South African Veterinary Association-Tydskrif Van Die Suid-Afrikaanse Veterinere Vereniging* 1992, 63(4):144-147.

Wang, S., Zheng, H., Tao, Z., Piessens, W. F., 1999. [Studies on recombinant chitinase and SXP-1 antigens as antimicrofilarial vaccines]. Zhongguo ji sheng chong xue yu ji sheng chong bing za zhi=Chinese journal of parasitology & parasitic diseases 17, 90-94.

Wright P F, Nilsson E, Van Rooij E M, Lelenta M, Jeggo M H: Standardisation and validation of enzyme-linked immunosorbent assay techniques for the detection of antibody in infectious disease diagnosis. *Rev Sci Tech* 1993, 12(2):435-450.

Wynne, E., Slocombe, J. O. D., Wilkie, B. N., 1981. Antigenic Analysis of Tissues and Excretory and Secretory Products from *Strongylus vulgaris*. Can. J. Comp. Med. 45, 259-265.

Wuertz D, members Rct, packages: ucbftfRc, gmm from Chauss P, gld from King R, gss from Gu C, nortest from Gross J, HyperbolicDist from Scott D, sandwich from Lumley T, Zeileis A et al: fBasics: Rmetrics—Markets and Basic Statistics. In., R package version 2110.79. edn; 2010.

Anonymous: Implementing Directive 2001/82/EC of the European Parliament and of the Council as regards the establishment of criteria for exempting certain veterinary medicinal products for food-producing animals from the requirement of a veterinary prescription In. Edited by Union E, vol. 2006/130/EF. Brussels; 2006. URL: http://eur-lex.europa.eu/LexUriServ/LexUriServ.do?uri=OJ:L:2006:349: 0015:01:EN:HTML Clustal Omega [http://www.ebi.ac.uk/Tools/msa/clustalo/] ExPASy Prosite [http://ca.expasy.org/prosite/]

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of diagnosing a *Strongylus vulgaris* infection in a subject during a prepatent period, comprising:
   (a) providing a biological sample from the subject; and
   (b) contacting the sample with a polypeptide comprising:
      the polypeptide of SEQ ID NO: 1 and/or a fragment thereof comprising at least 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, or 115 amino acid residues
      a polypeptide comprising an epitope of the polypeptide of SEQ ID NO: 1, wherein the epitope is selected from C-Ahx-FANAGSMTDAAI-amide (svar-1)(SEQ ID NO: 8) and/or C-AFAAFEKEIQSAQAQ-amide (svar-2)(SEQ ID NO: 9), or
      a combination thereof.

2. The method of claim 1, and further comprising detecting antibodies in the sample that specifically bind the polypeptide.

3. The method of claim 2, wherein the detection is conducted using an enzyme-linked immunosorbent assay (ELISA).

4. The method of claim 1, wherein the subject is diagnosed as being infected by migrating *S. vulgaris* larvae when antibodies that specifically bind the polypeptide are detected in the sample.

5. The method of claim 1, wherein the subject is a horse.

6. The method of claim 1, wherein the biological sample is a blood or serum sample.

7. A method of diagnosing a *Strongylus vulgaris* infection in a subject during a prepatent period, comprising:
 (a) providing a biological sample from the subject; and
 (b) contacting the sample with a purified antibody that specifically binds to an epitope of the polypeptide of SEQ ID NO: 1.

8. The method of claim 7, wherein the epitope comprises the amino acid residues of SEQ ID NO: 1 selected from C-Ahx-FANAGSMTDAAI-amide (svar-1)(SEQ ID NO: 8) and/or C-AFAAFEKEIQSAQAQ-amide (svar-2)(SEQ ID NO: 9).

9. The method of claim 7, and further comprising detecting a polypeptide in the sample to which the antibody specifically binds.

10. The method of a claim 9, wherein the subject is diagnosed as being infected by migrating *S. vulgaris* larvae when the polypeptide to which the antibody specifically binds is detected in the sample.

11. The method of claim 9, wherein the detection is conducted using an enzyme-linked immunosorbent assay (ELISA).

12. The method of claim 7, wherein the subject is a horse.

13. The method of claim 7, wherein the biological sample is a blood or serum sample.

* * * * *

SEQUENCE LISTING

```
<160> NUMBER OF SEQ ID NOS: 9

<210> SEQ ID NO 1
<211> LENGTH: 146
<212> TYPE: PRT
<213> ORGANISM: Strongylus vulgaris

<400> SEQUENCE: 1

Met Leu Lys Ile Val Ala Leu Ala Cys Leu Ala Val Ile Cys Leu Val
1               5                   10                  15

Lys Ala Gln Asn Gly Pro Pro Pro Phe Leu Gln Lys Ala Pro Ala Ala
            20                  25                  30

Val Gln Lys Glu Phe Glu Gly Leu Phe Ala Asn Ala Gly Ser Met Thr
        35                  40                  45

Asp Ala Ala Ile Asp Lys Met Val Lys Asp Trp Val Ala Lys Gln Ser
    50                  55                  60

Ala Glu Ile Lys Thr Ala Phe Ala Ala Phe Glu Lys Glu Ile Gln Ser
65                  70                  75                  80

Ala Gln Ala Gln Gly Glu Ala Ala His Gln Ala Ala Ile Ala Lys Phe
            85                  90                  95

Ser Pro Ala Ala Lys Glu Ala Asp Ala Lys Leu Thr Ala Ile Ala Asn
            100                 105                 110

Asp Arg Ser Lys Thr Asn Ala Gln Lys Gly Ala Glu Ile Asp Gly Ile
        115                 120                 125

Leu Lys Ala Leu Pro Glu Lys Val Arg Lys Glu Ile Glu Asp Ala Met
    130                 135                 140

Lys Gly
145

<210> SEQ ID NO 2
<211> LENGTH: 69
<212> TYPE: PRT
<213> ORGANISM: Cylicostephanus goldi

<400> SEQUENCE: 2

Met Leu Lys Ile Val Ala Leu Ala Cys Leu Ala Val Ile Cys Leu Ala
1               5                   10                  15

Gln Ala Gln Gln Gly Pro Pro Pro Phe Leu Ala Ser Ala Pro Pro Ala
            20                  25                  30
```

```
Val Gln Lys Glu Phe Glu Gly Leu Phe Ala Asn Ala Asp Lys Met Thr
             35                  40                  45

Asp Ala Glu Ile Asp Lys Met Val Lys Asp Trp Ile Gly Lys Gln Ser
 50                  55                  60

Asp Ala Val Lys Thr
 65

<210> SEQ ID NO 3
<211> LENGTH: 146
<212> TYPE: PRT
<213> ORGANISM: Necator americanus

<400> SEQUENCE: 3

Met Leu Lys Leu Val Ala Leu Val Cys Leu Ala Ile Cys Phe Ala
 1               5                  10                  15

Gln Gly Pro Gln Gly Pro Pro Phe Leu Gln Ser Ala Pro Ala Ala
             20                  25                  30

Val Gln Gln Asp Phe Asp Lys Leu Phe Val Asn Ala Gly Ser Lys Thr
             35                  40                  45

Asp Ala Glu Ile Asp Lys Met Val Gln Asp Trp Val Gly Lys Gln Asp
 50                  55                  60

Ala Ser Ile Lys Thr Ala Phe Asp Ala Phe Val Lys Glu Val Lys Ala
 65                  70                  75                  80

Ala Gln Ala Gln Gly Glu Ala Ala His Gln Ala Ala Ile Ala Lys Phe
                 85                  90                  95

Ser Ala Glu Ala Lys Ala Ala Asp Ala Lys Leu Ser Ala Ile Ala Asn
                100                 105                 110

Asp Arg Ser Lys Thr Asn Ala Gln Lys Gly Ala Glu Ile Asp Ser Val
                115                 120                 125

Leu Lys Gly Leu Pro Pro Asn Val Arg Thr Glu Ile Glu Asn Ala Met
                130                 135                 140

Lys Gly
145

<210> SEQ ID NO 4
<211> LENGTH: 147
<212> TYPE: PRT
<213> ORGANISM: Ancylostoma caninum

<400> SEQUENCE: 4

Met Leu Lys Leu Val Ala Leu Ala Cys Leu Ala Ile Cys Leu Ala
 1               5                  10                  15

Gln Gly Gly Pro Glu Gly Pro Pro Phe Leu Lys Ser Ala Pro Pro
             20                  25                  30

Glu Lys Val Thr Glu Phe Asp Ala Leu Phe Ala Asp Ala Gly Gly Leu
             35                  40                  45

Thr Asp Ala Gln Ile Asp Ala Lys Val Lys Gly Trp Ile Gly Lys Gln
 50                  55                  60

Ser Gln Asp Ile Gln Ser Ala Phe Asn Ala Phe Glu Ser Glu Val Lys
 65                  70                  75                  80

Ala Ala Gln Gln Gln Gly Glu Gln Ala His Gln Ala Val Ala Lys
                 85                  90                  95

Phe Ser Ala Glu Ala Lys Ala Ala Asp Ala Lys Leu Thr Ala Ile Ala
                100                 105                 110

Asn Asp Ala Ser Lys Thr Asn Ala Gln Lys Gly Ala Glu Ile Asp Ala
                115                 120                 125
```

-continued

```
Val Leu Lys Gly Leu Pro Gln Lys Val Arg Asp Glu Ile Glu Asn Ala
        130                 135                 140

Met Lys Gly
145

<210> SEQ ID NO 5
<211> LENGTH: 146
<212> TYPE: PRT
<213> ORGANISM: Ascaris suum

<400> SEQUENCE: 5

Met Lys Val Leu Ile Ile Phe Val Ala Ile Val Ile Ala Phe Ala
1               5                   10                  15

Gln Gly Pro Gln Gly Pro Pro Phe Leu Val Gly Ala Pro Ala Asn
                20                  25                  30

Val Val Ala Glu Phe Lys Gln Ile Ile Thr Gly Ala Pro Asp Lys Thr
            35                  40                  45

Asp Ala Glu Ile Asp Arg Asp Ile Glu Asn Trp Val Ala Arg Gln Gly
        50                  55                  60

Pro Lys Ile Lys Thr Glu Phe Asn Lys Phe Lys Thr Gln Met Gln Gln
65                  70                  75                  80

Gly Lys Ala Arg Ala Glu Ala Ala His Arg Ala Ser Ile Ala Lys Phe
                85                  90                  95

Ser Pro Ala Ala Lys Ala Ala Asp Ala Gln Leu Thr Ala Ile Ala Asp
                100                 105                 110

Asn Pro Asn Leu Lys Gly Arg Glu Lys Gln Gln Lys Ile Thr Gly Leu
            115                 120                 125

Leu Gln Ser Leu Pro Ala Ala Val Gln Ala Glu Phe Gln Lys Glu Met
        130                 135                 140

Gln Gly
145

<210> SEQ ID NO 6
<211> LENGTH: 146
<212> TYPE: PRT
<213> ORGANISM: Ascaris lumbricoides

<400> SEQUENCE: 6

Met Lys Val Leu Ile Ile Phe Phe Ala Ile Val Ile Ala Phe Ala
1               5                   10                  15

Gln Gly Pro Gln Gly Pro Pro Phe Leu Val Gly Ala Pro Ala Asn
                20                  25                  30

Val Val Ala Glu Phe Lys Gln Ile Ile Thr Gly Ala Pro Asp Lys Thr
            35                  40                  45

Asp Ala Glu Ile Asp Arg Asp Ile Glu Asn Trp Val Ser Arg Gln Gly
        50                  55                  60

Pro Lys Ile Lys Thr Glu Phe Asn Lys Phe Lys Thr Gln Met Gln Gln
65                  70                  75                  80

Gly Lys Ala Arg Ala Glu Ala Ala His Gln Ala Ser Ile Ala Lys Phe
                85                  90                  95

Ser Pro Ala Ala Lys Thr Ala Asp Ala Gln Leu Thr Ala Ile Ala Asp
                100                 105                 110

Asn Pro Asn Leu Lys Gly Arg Glu Lys Gln Gln Lys Ile Thr Ser Leu
            115                 120                 125
```

```
Leu Gln Ser Leu Pro Ala Ala Val Gln Ala Glu Leu Gln Lys Glu Met
    130                 135                 140

Gln Gly
145

<210> SEQ ID NO 7
<211> LENGTH: 131
<212> TYPE: PRT
<213> ORGANISM: Parascaris equorum

<400> SEQUENCE: 7

Leu Ile Ile Phe Ile Ala Ile Ala Gly Ile Ala Phe Ala Gln Gly Gln
1               5                   10                  15

Gln Gly Glu Gln Gly Pro Pro Pro Phe Leu Val Gly Ala Pro Ala Lys
            20                  25                  30

Val Val Ala Glu Phe Lys Gln Leu Val Asn Gly Ala Pro Asp Lys Thr
        35                  40                  45

Asp Ala Glu Val Asp Arg Asp Ile Glu Asn Trp Ile Ala Arg Gln Glu
    50                  55                  60

Pro Lys Val Lys Thr Glu Phe Asn Lys Phe Lys Thr Gln Met Arg Phe
65                  70                  75                  80

Ser Pro Ala Ala Lys Ala Ala Asp Ala Gln Leu Thr Ala Ile Ala Asp
                85                  90                  95

Asn Pro Asn Leu Lys Gly Arg Glu Lys Gln Gln Lys Ile Thr Ser Leu
            100                 105                 110

Leu Gln Ser Leu Pro Ala Ala Val Gln Ala Glu Leu Gln Lys Glu Met
        115                 120                 125

Gln Gly Thr
    130

<210> SEQ ID NO 8
<211> LENGTH: 13
<212> TYPE: PRT
<213> ORGANISM: Strongylus vulgaris
<220> FEATURE:
<221> NAME/KEY: X
<222> LOCATION: (1)..(1)
<223> OTHER INFORMATION: X is Ahx

<400> SEQUENCE: 8

Xaa Phe Ala Asn Ala Gly Ser Met Thr Asp Ala Ala Ile
1               5                   10

<210> SEQ ID NO 9
<211> LENGTH: 15
<212> TYPE: PRT
<213> ORGANISM: Strongylus vulgaris

<400> SEQUENCE: 9

Ala Phe Ala Ala Phe Glu Lys Glu Ile Gln Ser Ala Gln Ala Gln
1               5                   10                  15
```